(12) United States Patent
Nicolas et al.

(10) Patent No.: US 11,291,474 B2
(45) Date of Patent: Apr. 5, 2022

(54) SKIN TREATMENT TOOL APPLICATOR TIP

(71) Applicants: Ed F. Nicolas, Signal Hill, CA (US);
William Cohen, Los Alamitos, CA (US)

(72) Inventors: Ed F. Nicolas, Signal Hill, CA (US);
William Cohen, Los Alamitos, CA (US)

( * ) Notice: Subject to any disclaimer, the term of this patent is extended or adjusted under 35 U.S.C. 154(b) by 0 days.

(21) Appl. No.: 16/992,823

(22) Filed: Aug. 13, 2020

(65) Prior Publication Data

US 2021/0204982 A1 Jul. 8, 2021

Related U.S. Application Data

(60) Provisional application No. 62/957,707, filed on Jan. 6, 2020.

(51) Int. Cl.
*A61B 17/54* (2006.01)
*A61B 17/00* (2006.01)
*A61B 17/32* (2006.01)

(52) U.S. Cl.
CPC .. *A61B 17/545* (2013.01); *A61B 2017/00761* (2013.01); *A61B 2017/320004* (2013.01); *A61B 2217/005* (2013.01)

(58) Field of Classification Search
CPC ........ A61M 35/003; A61M 2037/0007; A61B 2017/00747; A61B 2017/00761;
(Continued)

(56) References Cited

U.S. PATENT DOCUMENTS

| | | | | |
|---|---|---|---|---|
| 2007/0156124 A1* | 7/2007 | Ignon | ........... | A61M 1/962 606/9 |
| 2007/0239173 A1* | 10/2007 | Khalaj | ........... | A61B 17/545 606/131 |
| 2009/0192442 A1* | 7/2009 | Ignon | ........... | A61B 17/54 604/22 |

* cited by examiner

*Primary Examiner* — Diane D Yabut
*Assistant Examiner* — Christian D Knauss
(74) *Attorney, Agent, or Firm* — Fulwider Patton LLP

(57) ABSTRACT

The present invention is an applicator tip for a hand piece assembly used in dermal abrasion procedures, the applicator tip having a cap shape with a plurality of apertures that form ports communicating with a fluid supply line in the hand piece assembly and a vacuum source to remove the abrading fluid. The fluid is introduced onto the outer abrading surface of the applicator tip through a first central aperture and spreads out along the outer abrading surface when the applicator tip is placed against the patient's skin. Recesses in the outer abrading surface establish pathways for the abrading fluid to move along as the applicator tip is moved over the patient's skin. The fluid emitting from the central port is moved into one of four quadrants defined by recesses in the outer abrading surface, each quadrant serving as a fluid chamber that receives fluid from the central fluid supply port. Each sector shaped chamber includes within its border a C-shaped barrier with its opening facing a dividing sector wall. As the applicator tip forms a seal with the patient's skin, fluid is introduced through the supply port and through the entrance of the chamber, filling each chamber with working fluid as the working fluid flows to and around the C-shaped barrier. Disposed inside each C-shaped barrier is a respective vacuum port that removes the working fluid from each chamber. Fluid from each chamber is vacuumed through its vacuum port after having flowed around a maze-like path, navigating the C-shaped barrier and sector walls in a vortex flow pattern.

5 Claims, 2 Drawing Sheets

(58) Field of Classification Search
CPC ....... A61B 2017/320004; A61B 2017/320008; A61B 2017/320012; A61B 2217/005; A61N 5/0616

See application file for complete search history.

SKIN TREATMENT TOOL APPLICATOR TIP

CROSS-REFERENCES TO RELATED APPLICATIONS

This application claims priority to U.S. Provisional Patent Application No. 62/957,707, filed Jan. 6, 2020, the content of which is incorporated herein by reference in its entirety.

BACKGROUND

The present invention relates to skin treatment tools, and more particularly to a disposable applicator tip to a micro dermabrasion handset that delivers a fluid through a first port and vacuums the fluid through a plurality of peripheral ports.

U.S. Pat. No. 8,048,089 describes a system for treating skin using an apparatus with a removable, disposable tip, the content of which is incorporated herein by reference. Whereas the tip of the U.S. Pat. No. 8,048,089 is spiral, it does not maximize the residency of the fluid on the skin and is less efficient at removing the fluid. Moreover, there is a high ratio of negative surface area to negative pressure with the device of the U.S. Pat. No. 8,048,089. That is, with a single vacuum port the amount of negative pressure to move the entire surface area is distributed over a small area, increasing the opportunity for skin damage. The present invention is intended to improve on the system of the U.S. Pat. No. 8,048,089 with an improved disposable applicator tip that increases residency time of the working fluid and more efficiently and safely removes the working fluid from the dermal surface.

SUMMARY OF THE INVENTION

The present invention is an applicator tip for a hand piece assembly having a cap shape with a circumferential edge and an outer abrading surface. The outer abrading surface includes a plurality of apertures that form ports communicating with a fluid supply line in the hand piece assembly and a vacuum source to remove the abrading fluid. The fluid is introduced onto the outer abrading surface of the applicator tip through a first central aperture and spreads out along the outer abrading surface when the applicator tip is placed against the patient's skin. Recesses in the outer abrading surface establish pathways for the abrading fluid to move along as the applicator tip is moved over the patient's skin. This motion of the applicator tip along the patient's skin, in combination with the moving fluid circulating on the applicator tip's outer abrading surface, provides the conditions under which skin cells may be sloughed off gently but effectively by the device.

In the present embodiment, the fluid emitting from the central port is moved into one of four quadrants defined by recesses in the outer abrading surface, each quadrant serving as a fluid chamber that receives fluid from the central fluid supply port. It should be noted that the number of chambers is not essential, and that three, five, or six chambers would work as well. Each fluid chamber has a fluid path beginning at the exit of the fluid supply port from the supply port into one of the sector shaped chambers. Each sector shaped chamber includes within its border a C-shaped barrier with its opening facing a dividing sector wall. As the applicator tip forms a seal with the patient's skin, fluid is introduced through the supply port and through the entrance of the chamber, filling each chamber with working fluid as the working fluid flows to and around the C-shaped barrier. Disposed inside each C-shaped barrier is a respective vacuum port that removes the working fluid from each chamber. Fluid from each chamber is vacuumed through its vacuum port after having flowed around a maze-like path, navigating the C-shaped barrier and sector walls in a vortex flow pattern. The present invention's use of four vacuum ports reduces the opportunity for a suction related injury by lowering the negative pressure requirements to provide a safer device.

These and other features of the present invention will best be understood with reference to the accompanying figures and the detailed description of the invention below.

DETAILED DESCRIPTION OF THE PREFERRED EMBODIMENTS

Figure 1:
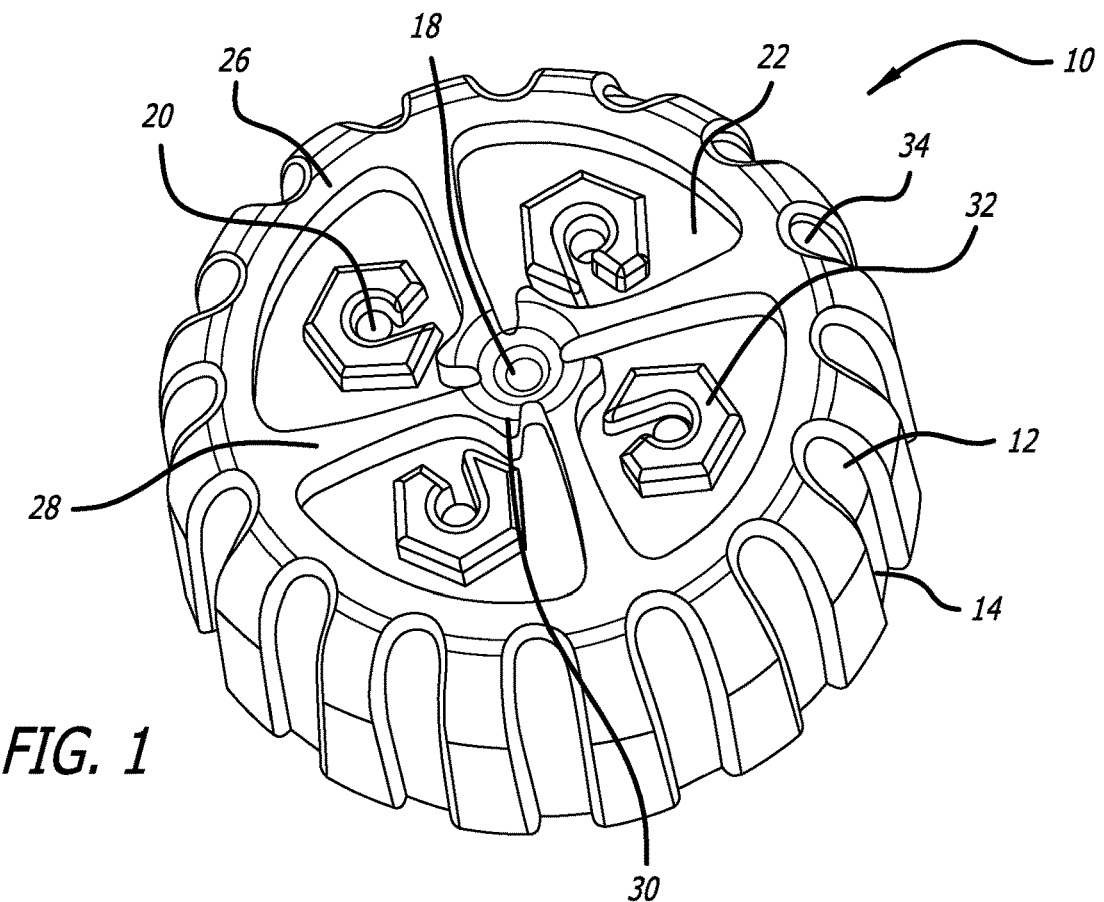
FIG. 1 is an elevated, perspective view of a first embodiment of an applicator tip of the present invention.
Figure 2:
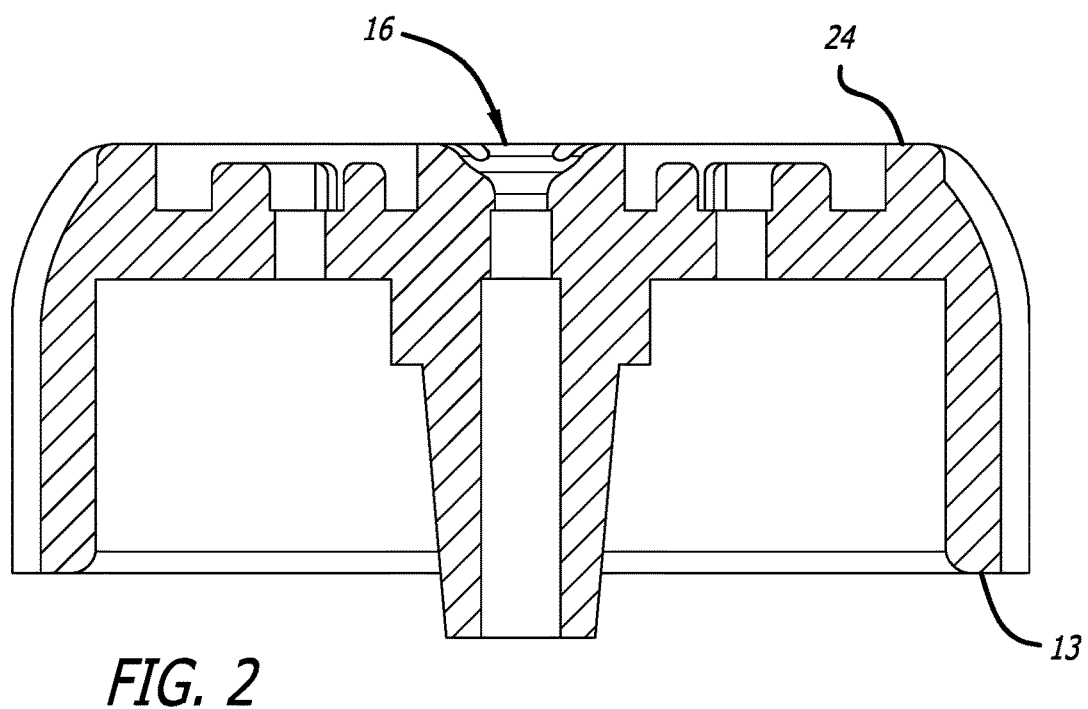
FIG. 2 is a cross sectional view of the applicator tip of FIG. 1.

FIGS. 1 and 2 illustrate a new disposable, removable tip 10 to a microdermabrasion hand piece. The disposable tip is formed in the shape of a cap (like a bottle cap) defining an interior space, and an exterior peripheral wall 12 formed with longitudinal recesses 14 for a more tactile response while applying and removing the tip 10. A central fluid channel 16 in the form of a tubular member is formed in the tip 10 beginning at a proximal end 13 and extending through the interior space to a central orifice 18 at the distal end. The central orifice 18 provides an outlet where fluid pumped through the tip 10 is introduced to an interface between the tip's distal surface and a patient's skin. Four vacuum ports 20 arrayed radially from the central orifice and circumferentially spaced from each other remove the fluid introduced at the central orifice 18. Each vacuum port 20 is located in a recessed sector 22 of the distal surface 24 of the tip 10 that are defined by a circumferential ridge or wall 26 and substantially radially inwardly oriented walls 28 from the circumferential wall, as illustrated in FIG. 1. The walls 28 terminate at the central orifice 18 and cooperate to form an opening 30 about the central orifice where fluid is delivered into one of the four sectors 22.

Each vacuum port 20 is substantially surrounded by a C-shaped barrier 32 having a height consistent with, or slightly below, the circumferential ridge 26 and the radially inwardly oriented walls 28. The height of the C-shaped barrier 32 allows the patient's skin to flex when pulled by the vacuum ports 20, which in turn brings the skin in contact with the edges of the quadrant borders 26, 28 to abrade the skin. It is important that the borders of the quadrant 22 and the barriers 32 allow a vacuum seal to be formed against the patient's skin from the negative pressure of the vacuum ports 20. Fluid 34 entering the central orifice flow into each quadrant 22 through a narrow opening 30 formed between the ends of the radially inwardly oriented extensions 28, and begin to fill the quadrants 22 with the fluid 34. The shape and position of the C-shaped barriers 32 establish a preferred flow direction using a path of least resistance to preferentially move the fluid 34 along an elongated arc to the vacuum port 20. To maximize the distance traveled by the fluid, the C shaped barrier 32 may open toward an adjacent radial wall 28. The vacuum ports 20 draw the fluid 34 out of the sector using the negative pressure in the closed space between the patient's skin and the borders 26, 28 of the sector 22, moving the fluid 34 into the sector and around the barrier 32 before exiting the sector through the vacuum port 20 so as to be collected outside of the hand piece. To remove the fluid 34, a substantially airtight seal is formed by the wet distal surfaces of the tip (circumferential wall, radially oriented walls, and C-shaped barriers) and the wet skin of the patient, reducing the level of vacuum needed to remove the fluid. Since the four vacuum ports 20 cooperate to remove the fluid 34 from the central orifice 18, each vacuum port 20 requires less negative pressure than the prior art where a single or dual vacuum ports are disclosed.

During treatment, a vacuum is applied to the hand piece (not shown) resulting to the patient's skin being drawn against the distal surfaces of the tip's four quadrants. During this condition, a treatment fluid 34 is dispensed from the central orifice 18 of the tip 10, wetting and lubricating the skin and its pores while the skin is in a dilated stage. A negative pressure is applied to the tip 10 at the vacuum ports 20, whereupon the tip 10 is moved and rotated over the surface of the skin resulting to improved exfoliation, abrasion, stimulation or angulation of the skin.

The use of quadrants 22 (or other radially defined shapes) increase the extraction/hydration efficiency and minimize cross contamination. Contrast with prior art devices that have longer fluid return paths that promote a possibility of exposing the used fluid to open/dilated pores, the present invention minimizes such opportunity for contamination without the need for a higher vacuum level. Moreover, the turbulent swirling action of the fluid on the skin's surface due to the C-shaped barrier 32 results in a higher fluid velocity and better exfoliation of the skin. That is, the greater the fluid velocity, the better the fluid overcomes any surface tension and therefore results in higher skin absorption of fluid during the dilated stage of the skin pores. The turbulent swirling effect also increases the residence time of fluid on the skin, resulting in better absorption and better utilization of the fluid. Finally, the combination of the abrupt distal edges and swirling fluid/vacuum action results to more efficient dislodging of clogged skin pores, and extracting the sebum axially. Conversely, the prior art dislodges clogged skin pores in a radial direction.

Figure 3A:
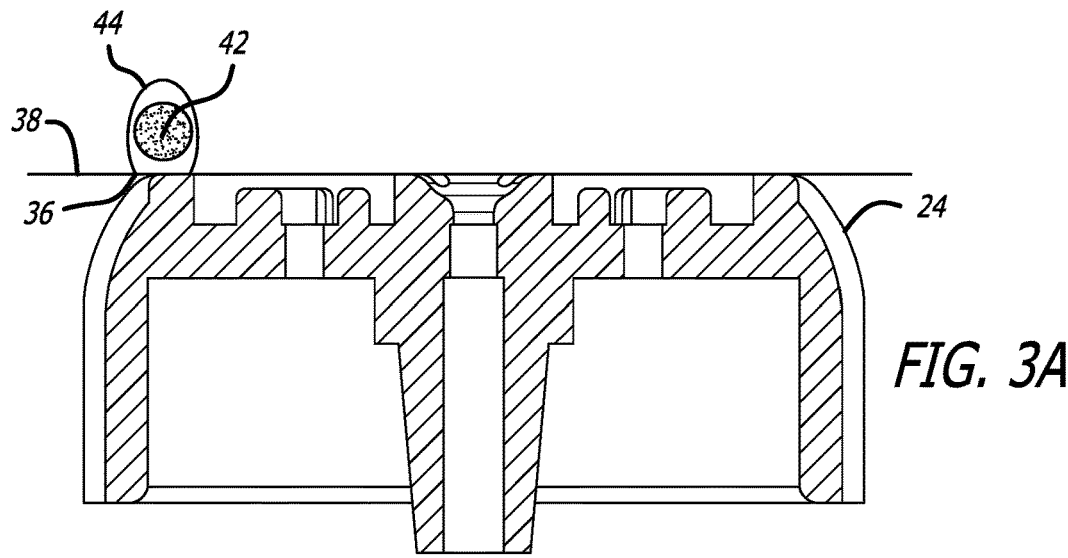
FIG. 3A is a cross sectional view of the applicator tip in contact with a pore on the skin.
Figure 3B:
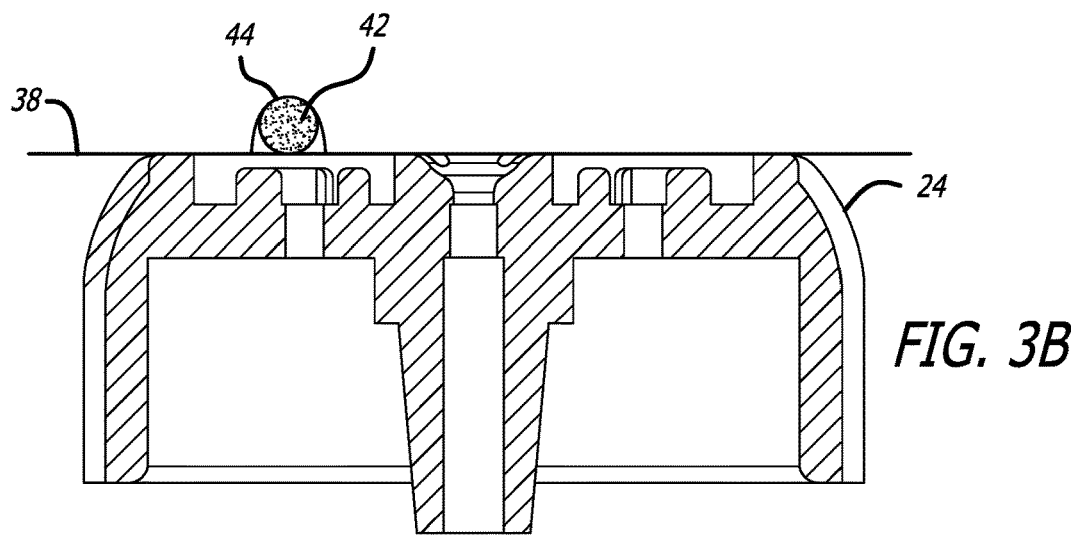
FIG. 3B is a cross sectional view of the applicator tip flushing an exposed pore.
Figure 3C:
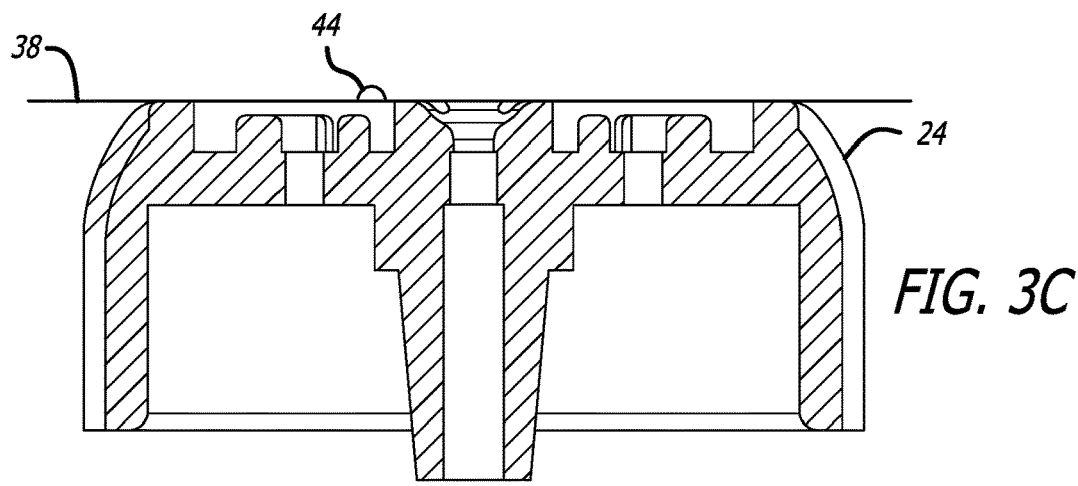
FIG. 3C is a cross sectional view of the applicator tip evacuating the exposed pore.

FIG. 3 illustrates the process whereby the present invention is used to treat the surface of a patient's skin. One can observe the interface 36 between the patient's skin 38 and the distal surface 24 of the tip 10, where a pore on the skin is shown in significant exaggeration for illustrative purposes. In the first stage of the process, a patient's skin 38 with a clogged pore 42 has the tip 10 of the present invention moved over its surface such that the dermis 44 covering of the clogged pore 42 is abraded by the tip's distal abrupt surfaces 24. The now exposed pore 42 in stage 2 is flushed with the fluid as the tip 10 moves over the surface of the skin 38, and the vacuum port 20 draws the fluid 34 and the contents of the pore through the tip 10 and into the hand piece. Some fluid remains in the pore to disinfect and clean the pore 42, leaving the skin hydrated and free of clogs and dirt.

While specific geometries, shapes, and numbers have been disclosed, the invention is not limited to any such specific embodiment. For example, the quadrants of the distal surface can be substituted into tripartite or five or more sectors without departing from the scope of the invention. Similarly, the shape of the barrier around the vacuum port can vary as long as there is a preferred flow direction of the fluid exiting the central aperture. Other such substitutions and modifications will readily be appreciated by those of ordinary skill in the art, and such substitutions and modifications are intended to be included within the scope of the invention.

We claim:

1. An applicator tip for a dermal abrasion hand piece, comprising:
a cap shaped body defining an interior space, an exterior peripheral wall, and an exterior distal surface, the exterior distal surface having a central channel extending from the interior space, and a plurality of sector shaped cavities enclosed by radial walls terminating at a circumferential wall, the sector shaped cavities fluidly connected to the central channel, and each sector shaped cavity including a vacuum port centrally disposed therein that extends to the interior space, and a C-shaped column confined inside the sector shaped cavity and surrounding the respective vacuum port;
wherein an opening of the C-shaped column faces away the central channel.

2. The applicator tip of claim 1, having four sector shaped cavities.

3. The applicator tip of claim 1, wherein each opening of the C-shaped columns opens toward an adjacent radial wall.

4. The applicator tip of claim 1, wherein the radial walls, the circumferential wall, and the C-shaped columns all have a common height.

5. The applicator tip of claim 1, further comprising a tubular structure extending from the central channel through and outside the interior space.

* * * * *